US008823792B2

(12) United States Patent
Omi (10) Patent No.: US 8,823,792 B2
(45) Date of Patent: Sep. 2, 2014

(54) WAKEFULNESS LEVEL ESTIMATION APPARATUS

(75) Inventor: Takuhiro Omi, Anjo (JP)

(73) Assignees: Toyota Jidosha Kabushiki Kaisha, Toyota-shi (JP); Denso Corporation, Kariya-shi (JP)

( * ) Notice: Subject to any disclaimer, the term of this patent is extended or adjusted under 35 U.S.C. 154(b) by 1016 days.

(21) Appl. No.: 12/428,745

(22) Filed: Apr. 23, 2009

(65) Prior Publication Data
US 2009/0268022 A1 Oct. 29, 2009

(30) Foreign Application Priority Data

Apr. 23, 2008 (JP) ................................. 2008-112860

(51) Int. Cl.
*H04N 7/18* (2006.01)
*G08B 21/06* (2006.01)
*A61B 5/18* (2006.01)

(52) U.S. Cl.
CPC .. *G08B 21/06* (2013.01); *A61B 5/18* (2013.01)
USPC ........... 348/135; 340/576; 340/575; 600/544; 600/558; 600/300; 382/104; 382/209

(58) Field of Classification Search
USPC ........... 348/135; 600/300, 544, 558; 382/104, 382/209; 340/576, 575
See application file for complete search history.

(56) References Cited

U.S. PATENT DOCUMENTS

| 5,488,353 | A  | * | 1/1996  | Kawakami et al. ........... 340/576 |
| 6,337,629 | B1 | * | 1/2002  | Bader ............................ 340/576 |
| 6,625,485 | B2 | * | 9/2003  | Levendowski et al. ....... 600/544 |
| 6,661,345 | B1 | * | 12/2003 | Bevan et al. .................. 340/575 |
| 2002/0128751 | A1 | * | 9/2002  | Engstrom et al. ................ 701/1 |
| 2003/0181822 | A1 | * | 9/2003  | Victor .......................... 600/558 |
| 2004/0234103 | A1 | * | 11/2004 | Steffein ........................ 382/104 |
| 2005/0163383 | A1 | * | 7/2005  | Kim et al. ..................... 382/209 |
| 2006/0038689 | A1 | * | 2/2006  | Ikegami et al. ............... 340/575 |
| 2008/0180257 | A1 | * | 7/2008  | Omi et al. ..................... 340/575 |
| 2008/0291032 | A1 | * | 11/2008 | Prokhorov et al. ........... 340/576 |
| 2009/0048737 | A1 |   | 2/2009  | Nakagoshi et al. |
| 2010/0076273 | A1 | * | 3/2010  | Shigetou ...................... 600/300 |

FOREIGN PATENT DOCUMENTS

| JP | 07-257220 A | 10/1995 |
| JP | 11339200 | 12/1999 |
| JP | 3638980 | 4/2005 |
| JP | 2006109980 | 4/2006 |
| JP | 2007117608 | 5/2007 |
| JP | 2008-188108 A | 8/2008 |
| JP | 2009-087122 A | 4/2009 |

* cited by examiner

*Primary Examiner* — Thuong Nguyen
(74) *Attorney, Agent, or Firm* — Gifford, Krass, Sprinkle, Anderson & Citkowski, P.C.

(57) ABSTRACT

A wakefulness level estimation apparatus includes: an estimation portion that estimates a level of wakefulness of a subject person based on one of a wakefulness level estimation function, of which a variable is a wakefulness level correlation value of the subject person, and a difference between the wakefulness level correlation value of the subject person and a reference value of the wakefulness level correlation value; a stimulation detection portion that detects whether an awakening stimulation is externally applied to the subject person; and a correction portion that, when the stimulation detection portion detects that the awakening stimulation is applied to the subject person, performs a correction of one of the reference value of the wakefulness level correlation value and the wakefulness level estimation function, which is used for estimating the level of wakefulness of the subject person.

16 Claims, 6 Drawing Sheets

| LEVEL OF DROWSINESS | 0 | 1 | 2 | 3 | 4 | 5 |
|---|---|---|---|---|---|---|
| CRITERIA FOR DETERMINATION | EXTREMELY ALERT | ALERT | NEITHER ALERT NOR DROWSY | DROWSY, BUT NO EFFORT TO KEEP ALERT | VERY DROWSY, GREAT EFFORT TO KEEP ALERT | FALL ASLEEP |
| CHARACTERISTIC BEHAVIORS | QUICK AND FREQUENT EYE MOTION<br><br>STEADY BLINKING CYCLE<br><br>ACTIVE BLINKING MOTION ACCOMPANIED BY MOVEMENT OF BODY | SLOWER EYE MOTION<br><br>LIPS OPENED | SLOW AND FREQUENT BLINKING MOTION<br><br>MOUTH MOVED<br><br>YAWNING STARTED<br><br>CHANGE OF POSTURE ON SEAT AND MOVEMENT OF HAND TO FACE | INTENTIONAL BLINKING<br><br>SLOW BLINKING AND EYE MOTIONS<br><br>HEAD SHAKE<br><br>UNNECESSARY MOVEMENT OF ENTIRE BODY, SUCH AS MOVEMENT OF SHOULDERS UP AND DOWN<br><br>FREQUENT YAWNING AND OCCASIONAL DEEP BREATHING | EYELIDS CLOSED<br><br>HEAD INCLINES FORWARD<br><br>HEAD INCLINES BACKWARD | — |

WAKEFULNESS LEVEL ESTIMATION APPARATUS

INCORPORATION BY REFERENCE

The disclosure of Japanese Patent Application No. 2008-112860 filed on Apr. 23, 2008 including the specification, drawings and abstract is incorporated herein by reference in its entirety.

BACKGROUND OF THE INVENTION

1. Field of the Invention

The invention relates to a wakefulness level estimation apparatus that estimates a level of wakefulness of a person (subject person).

2. Description of the Related Art

Various types of apparatuses that estimate a state of wakefulness of a driver (subject person) have been proposed for the use in a driver assist system, etc. For example, Japanese Patent Application Publication No. 2006-109980 (JP-A-2006-109980) describes an apparatus that detects the degree of opening of an eye of a driver (hereinafter referred to as "eye-opening degree"), and determines a level of wakefulness of the driver based on a difference between the detected eye-opening degree and a reference value of the eye-opening degree. The reference value of the eye-opening degree is set based on data on the eye-opening degree (hereinafter referred to as "eye-opening degree data") taken when it is determined that the driver is awake, such as when the driver speaks or the driver consciously operates a vehicle.

However, even when the driver speaks or consciously operates the vehicle, it is still likely that the driver's level of wakefulness is low. If the reference value of the eye-opening degree is set based on the eye-opening degree data taken under such circumstances, the set reference value is not proper one, and therefore, it is not possible to estimate the level of wakefulness with high accuracy. Further, when the reference value of the wakefulness level correlation value and the wakefulness level estimation function, etc. are set by a statistical method, the results of estimation of the level of wakefulness vary among different individuals. Further, even when only one person is subjected to the estimation of the level of wakefulness, the estimation results intra-individually vary depending on, for example, personal conditions on the day of estimation. Further, if an actuation to awaken the driver (hereinafter referred to as "awakening actuation") is performed based on the estimation results thus obtained, timing at which the awakening actuation is performed may be delayed, or the awakening actuation may be unnecessarily performed.

SUMMARY OF THE INVENTION

The invention provides a wakefulness level estimation apparatus in which a level of wakefulness of a subject person is estimated with high accuracy.

A wakefulness level estimation apparatus according to the invention includes: an estimation portion that estimates a level of wakefulness of a subject person based on one of a wakefulness level estimation function, of which a variable is a wakefulness level correlation value of the subject person, and a difference between the wakefulness level correlation value of the subject person and a reference value of the wakefulness level correlation value; a stimulation detection portion that detects whether an awakening stimulation is externally applied to the subject person; and a correction portion that, when the stimulation detection portion detects that the awakening stimulation is applied to the subject person, performs a correction of one of the reference value of the wakefulness level correlation value and the wakefulness level estimation function, which is used for estimating the level of wakefulness of the subject person.

In the wakefulness level estimation apparatus, the stimulation detection portion detects whether a stimulation is externally applied to the subject person of the wakefulness level estimation is externally stimulated. When the subject person is externally stimulated, the level of wakefulness of the subject person is raised, and the wakefulness level correlation value accordingly changes. Therefore, in the wakefulness level estimation apparatus, when the stimulation detection portion detects that the stimulation is applied, the correction portion corrects the reference value of the wakefulness level correlation value or the wakefulness level estimation function. Then, the wakefulness level estimation apparatus estimates the level of wakefulness of the subject person based on the wakefulness level estimation function or the difference between the wakefulness level correlation value of the subject person and the reference value of the wakefulness level correlation value. In this way, in the wakefulness level estimation apparatus, when the subject person is externally stimulated (that is, when the level of wakefulness is certainly raised), the correction portion corrects the reference value of the wakefulness level correlation value or the wakefulness level estimation function, which is used for estimating the level of wakefulness, and therefore, it is possible to estimate the level of wakefulness with high accuracy by using the corrected reference value or the corrected wakefulness level estimation function.

The wakefulness level correlation value changes in accordance with the level of wakefulness of the subject person, and may be, for example, physiological information, such as blinking information, eye direction information, heart rate information, breathing information, brain wave information, and electro-dermal activity information. The externally applied stimulation is the stimulation externally applied that raises the level of wakefulness of the subject person, and examples of such an external stimulation include a stimulus provided by sound, light, and vibration, etc. In particular, when the driver is the subject person of the wakefulness level estimation, examples of the external stimulation include a stimulus produced due to the road circumstances, such as an electronic toll collection (hereinafter referred to as "ETC") gate in the ETC system that has been put into practice in Japan or traffic control.

According to the invention, it is possible to estimate the level of wakefulness with high accuracy by correcting at least one of the reference value of the wakefulness level correlation value and the wakefulness level estimation function, which are used for estimating the level of wakefulness of the subject person when the subject person is externally stimulated.

BRIEF DESCRIPTION OF THE DRAWINGS

The features, advantages, and technical and industrial significance of this invention will be described in the following detailed description of embodiment of the invention with reference to the accompanying drawings, in which like numerals denote like elements, and wherein.

DETAILED DESCRIPTION OF EMBODIMENT

An embodiment of a wakefulness level estimation apparatus according to the invention will be hereinafter described with reference to the attached drawings.

In the embodiment, the wakefulness level estimation apparatus according to the invention is employed as a drowsiness level estimation apparatus mounted on a vehicle. The drowsiness level estimation apparatus according to the embodiment estimates a level of drowsiness (that functions as a level of wakefulness) of a driver of the vehicle. In the drowsiness level estimation apparatus according to the embodiment, a plurality of blinking characteristic amounts (each functions as a wakefulness level correlation value) of the driver are detected at predetermined time intervals, and the driver's level of drowsiness is estimated based on a function for estimating the driver's level of drowsiness (hereinafter referred to as "drowsiness level estimation function"; this functions as wakefulness level estimation function) using the detected blinking characteristic amounts as variables. Further, when the estimated level of drowsiness reaches a level that may result in impairing driving operations (that is, when the driver's level of wakefulness is significantly decreased), the drowsiness level estimation apparatus according to the embodiment applies stimulus to the driver to awaken the driver.

Figure 1:
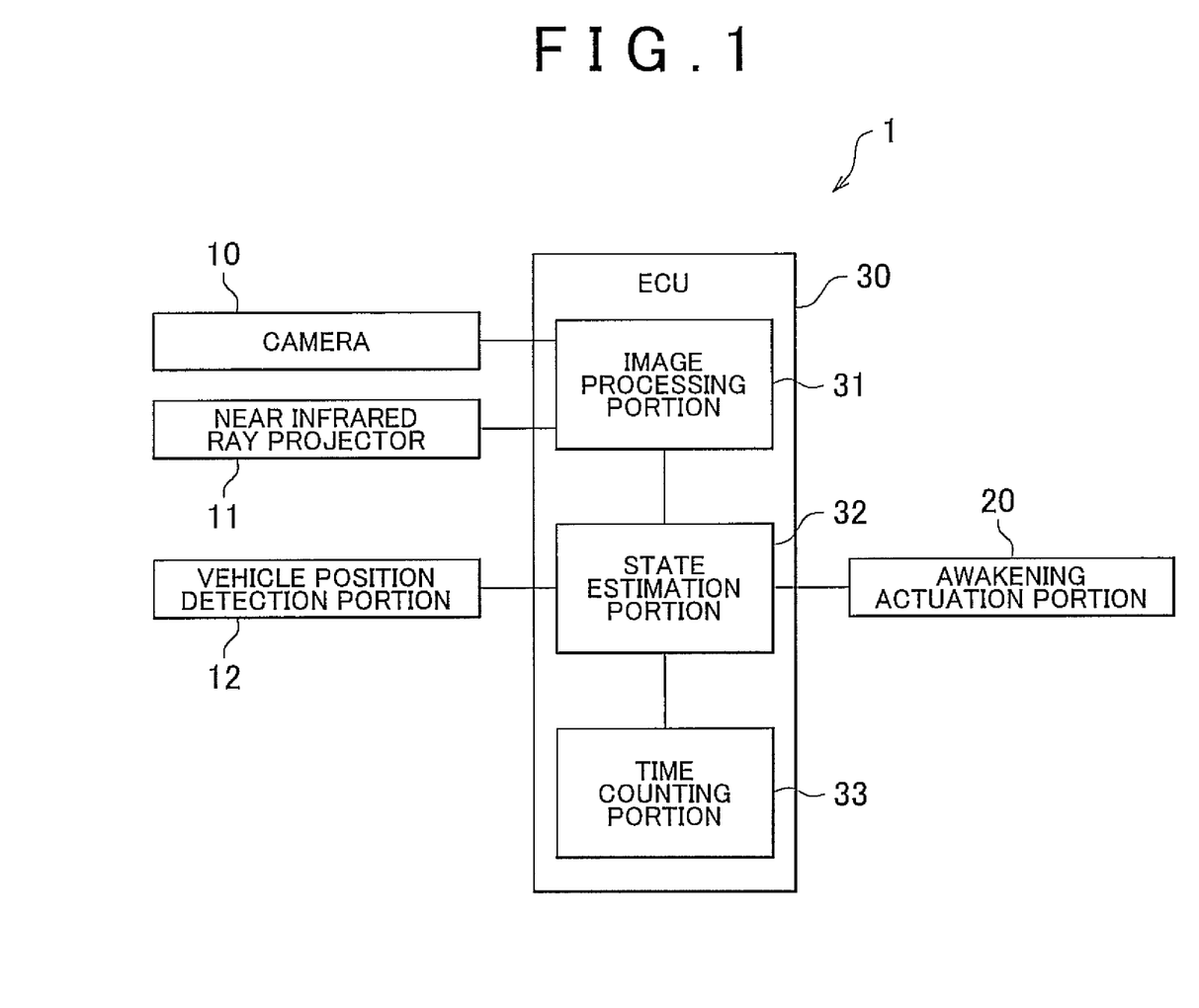
FIG. 1 shows the configuration of a drowsiness level estimation apparatus according to an embodiment of the invention.
Figure 2:
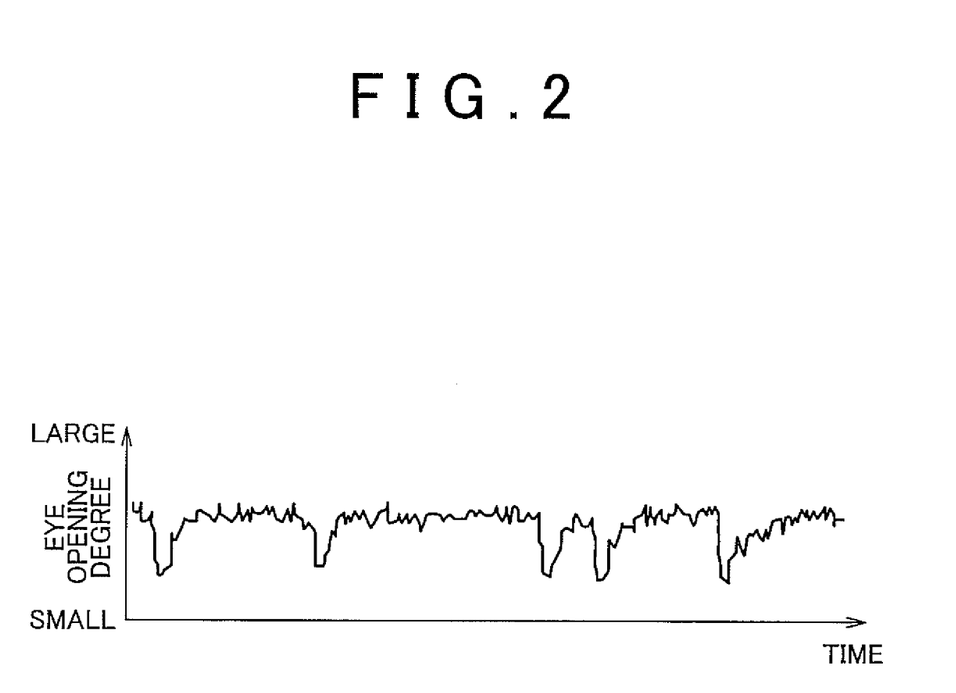
FIG. 2 is an example of time-series data on the eye-opening degree detected by an image processing portion shown in FIG. 1.
Figure 3:
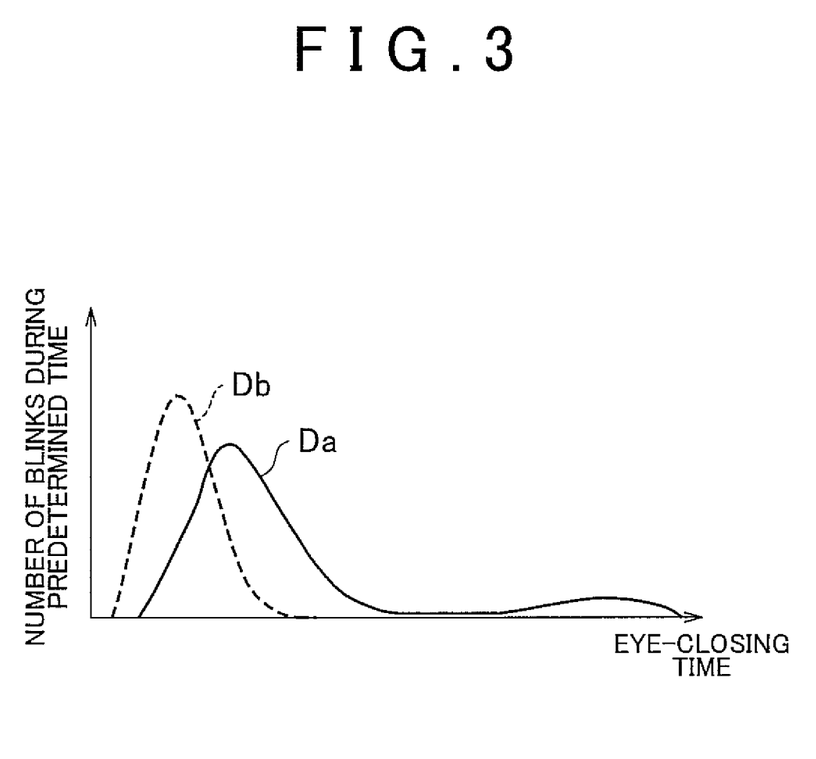
FIG. 3 is an example of a frequency distribution of eye-closing time per blink.
Figure 4:
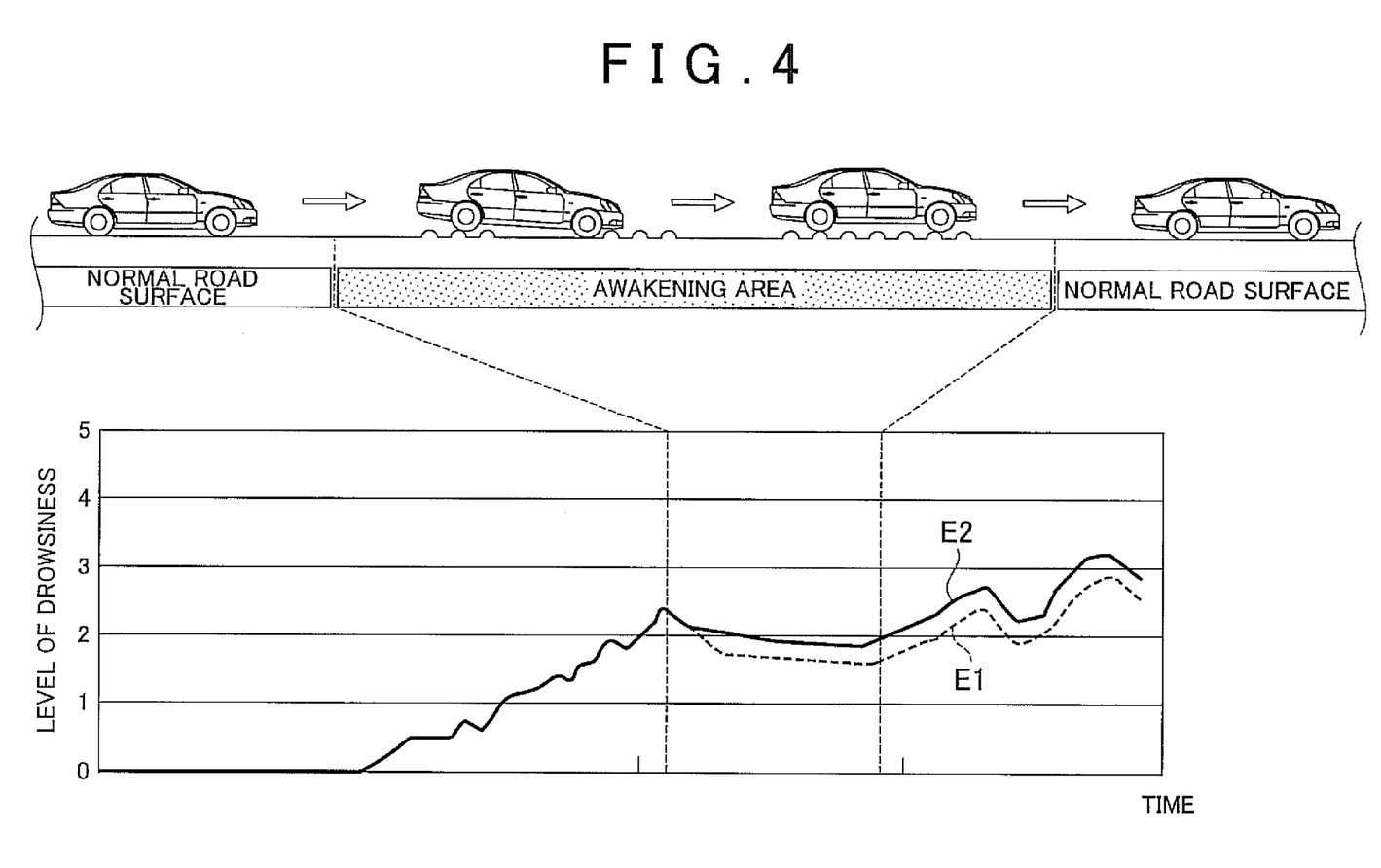
FIG. 4 is an example of results of estimation of a level of drowsiness.
Figure 5:
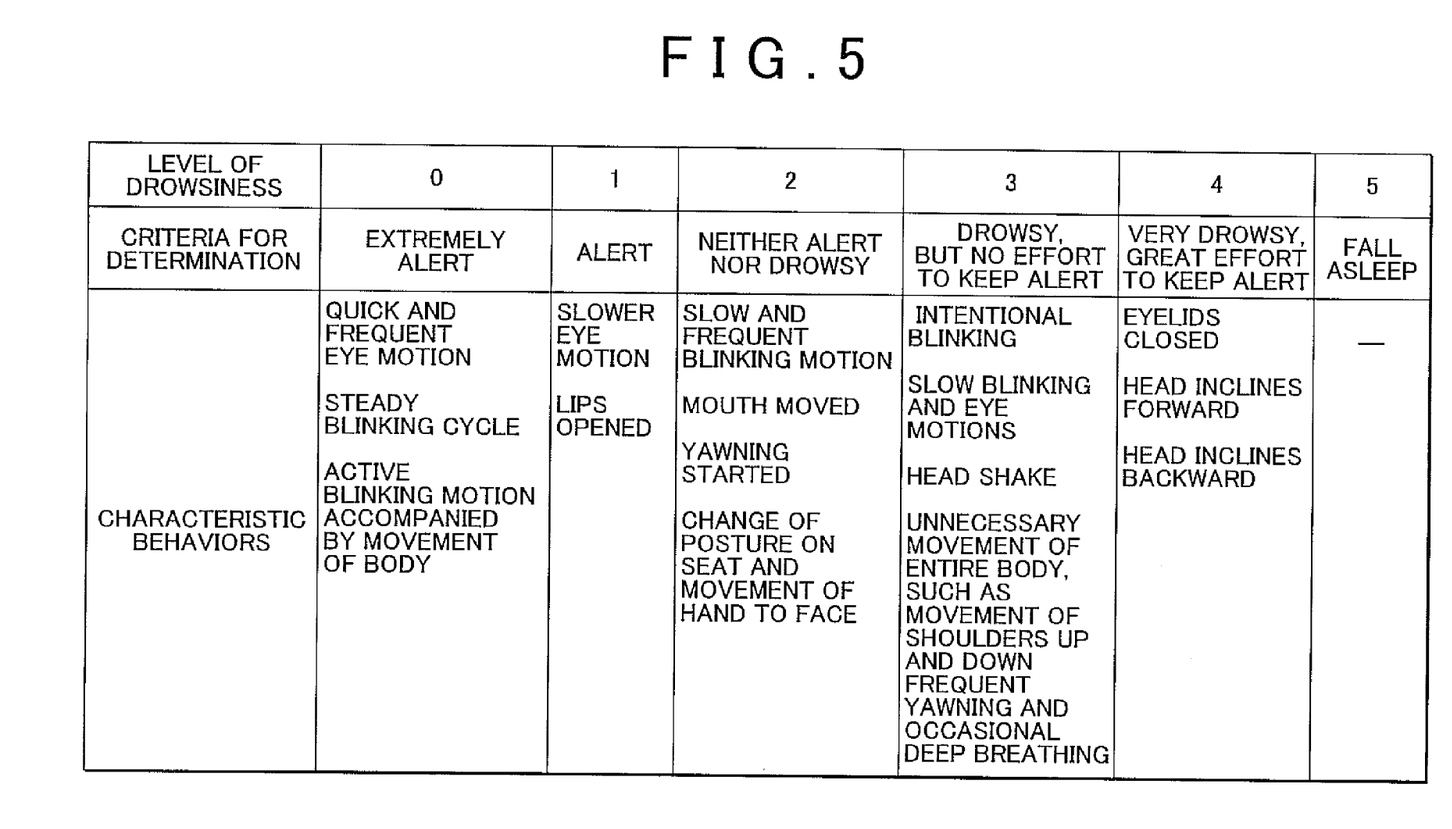
FIG. 5 is a table showing characteristics for each level of drowsiness.

Referring to FIGS. 1 to 5, a drowsiness level estimation apparatus 1 according to the embodiment will be described. FIG. 1 is a diagram showing the configuration of the drowsiness level estimation apparatus 1 according to the embodiment. FIG. 2 is an example of time-series data on the eye-opening degree (hereinafter referred to as "time-series eye-opening degree data") detected by an image processing portion 31 shown in FIG. 1. FIG. 3 is an example of a frequency distribution of eye-closing time per blink. FIG. 4 is an example of results of estimation of the level of drowsiness. FIG. 5 shows characteristics for each level of drowsiness.

In the drowsiness level estimation apparatus 1, the level of drowsiness is estimated using the drowsiness level estimation function when the vehicle runs in a section in which the driver of the vehicle is externally stimulated (the section will be hereinafter referred to as "awakening area"), and if the estimated level of drowsiness does not show that the awakening effect is produced, the drowsiness level estimation function is corrected in order to detect the level of drowsiness with high accuracy. The drowsiness level estimation apparatus 1 includes a camera 10, a near infrared ray projector 11, a vehicle position detection portion 12, an awakening actuation portion 20, and an electronic control unit (ECU) 30.

The camera 10 captures an image of a region including a face of the driver, and generates an image in accordance with luminance of light including near infrared rays. It is preferable that the camera 10 have a sufficient sensitivity to the wavelength of the light emitted and projected by the near infrared ray projector 11 in order to stably capture the image even at night. The camera 10 is attached to an instrument panel or to a steering column in a manner such that the camera 10 is aimed at the driver's face. The camera 10 is controlled to capture images at predetermined time intervals (for example, every 1/30 second), and outputs image information of each frame to the ECU 30.

The near infrared ray projector 11 projects near infrared rays toward a region around the driver's face in order for the camera 10 to capture clear images. The near infrared ray projector 11 is provided in proximity to the camera 10, and is aimed at the driver's face. The near infrared ray projector 11 projects the near infrared rays to the region around the driver's face while the camera 10 is operating. The camera 10 and the near infrared ray projector 11 are both activated when the drowsiness level estimation apparatus 1 is activated, and are stopped when the drowsiness level estimation apparatus 1 is stopped.

In the drowsiness level estimation apparatus 1 according to the embodiment, a near-infrared image-capturing means is used in order to avoid dazzling the driver by the light projected to stably capture images even at night.

The vehicle position detection portion 12 detects a present position of the vehicle, and may be, for example, a GPS receiver or a navigation system. The vehicle position detection portion 12 detects the present position of the vehicle at predetermined time intervals and transmits the detected position of the vehicle to the ECU 30.

The awakening actuation portion 20 performs an actuation to awaken the driver of the vehicle (hereinafter referred to as "awakening actuation"), and may be, for example, a portion that changes conditions of an air conditioner (to supply cold air, for example), a portion that vibrates a seat, a portion that retracts the seatbelt, a portion that vibrates the steering wheel, a warning portion, or a portion that informs the driver that the driver's level of wakefulness is low (for example, a display unit or a speaker). When the awakening actuation portion 20 receives an awakening actuation control signal from the ECU 30, the awakening actuation portion 20 is operated in accordance with the awakening actuation control signal. Further, if there is provided a button pressed by the driver when the driver is aware of the driver's own drowsiness and intends to increase the level of wakefulness, the awakening actuation portion 20 receives an ON signal from the button when the button is pressed and is operated in accordance with the ON signal.

The ECU 30 includes, for example, a central processing unit (CPU), a read-only memory (ROM), a random access memory (RAM), the image processing portion 31, and a time counting portion (timer) 33, and executes integrated control of the drowsiness level estimation apparatus 1. The ECU 30 receives images from the camera 10 and the information on the present position of the vehicle from the vehicle position detection portion 12 at predetermined time intervals. Then, in the ECU 30, the image processing portion 31 and a state estimation portion 32 perform processes to estimate the driver's level of drowsiness with the use of the received information at predetermined time intervals. Further, when the estimated level of drowsiness reaches a level that may result in impairing driving operations, the ECU 30 outputs the awakening actuation control signal to the awakening actuation portion 20.

In the embodiment, the processes performed by the vehicle position detection portion 12 and the state estimation portion 32 of the ECU 30 together function as a stimulation detection portion according to the invention, and the processes performed by the state estimation portion 32 of the ECU 30 function as a correction portion according to the invention.

Next, the image processing portion 31 will be described in detail. In the image processing portion 31, a region of the captured image in which an eye of the driver is captured is identified, and the region is extracted from the captured image (hereinafter referred to as "eye region image"). The method of identifying the eye region may be any method, and a commonly used method may be used. The image processing portion 31 detects the eye-opening degree based on the eye region image. FIG. 2 shows the time-series eye-opening degree data, and shows that the driver blinks at timings shown by portions in the graph that protrude downward because the eye-opening degree becomes small.

Next, the state estimation portion 32 will be described. The state estimation portion 32 receives the eye-opening degree from the image processing portion 31 at predetermined time intervals. The state estimation portion 32 sequentially buffers the time-series eye-opening degree data taken at predetermined time intervals for a past predetermined time before the current time point. Then, the state estimation portion 32 analyzes the time-series eye-opening degree data taken for a set time period, and extracts the plurality of blinking characteristic amounts. Examples of the blinking characteristic amounts include the eye-opening degree when the driver's eyes are open, an average eye-closing time per blink, an eye-closing time deviation, total eye-closing time during unit time, and the number of blinks.

FIG. 3 shows a frequency distribution with the horizontal axis indicating the eye-closing time per blink, and the vertical axis indicating the blinking frequency of each eye-closing time. A distribution Da shown by a solid line shows a case where the driver is drowsy, and a distribution Db shown by a dotted line shows a case where the driver is awake. As shown in FIG. 3, the distribution Da when the driver is drowsy shows that the eye-closing time per blink is long, and the standard deviation of the distribution Da is large. On the other hand, the distribution Db when the driver is awake shows that the eye-closing time per blink is short, and the standard deviation of the distribution Db is small. As exemplified in FIG. 3, the blinking characteristic amounts are significantly different between when the driver is drowsy and when the driver is awake. Therefore, it is possible to determine the level of drowsiness based on the blinking characteristic amounts.

On the basis of this, the level of drowsiness is estimated based on the drowsiness level estimation function using the plurality of blinking characteristic amounts as variables. The drowsiness level estimation function is a function shown below that is used to estimate the level of drowsiness, using the plurality of blinking characteristic amounts as variables.

Level of drowsiness $D=f_1$(eye-opening degree when the driver's eyes are open)$+f_2$(average eye-closing time per blink)$+f_3$(eye-closing time deviation)$+f_4$(total eye-closing time during unit time)$+f_5$(number of blinks)$+$ Each term of the function that is represented as $f_n$ has a corresponding coefficient, and the coefficients for the terms of the function are set to the default values when the vehicle operation is started, and are corrected as needed after the start of the vehicle operation. The default values for the coefficients are statistically obtained based on the blinking characteristic amount data and sensory evaluation values, which are taken from many examinees.

There is not any specific classification for the level of drowsiness D. In the present specification, however, the level of drowsiness is classified into the values of 0 to 5 that will be defined and described below. As shown in FIG. 5, when the level of drowsiness D is 0, it indicates that the driver is fully awake. In this case, the driver's eye motion is quick and frequent, the blinking cycle of the driver is steady, and blinking motion is active and accompanied by a movement of the driver's body. When the level of drowsiness D is 1, it indicates that the driver feels a little drowsy. In this case, the driver's eye motion becomes slower, and the driver's lips are open. When the level of drowsiness D is 2, it indicates that the driver is drowsy. In this case, the blinking motion is slow and frequent, the driver moves the driver's mouth, and the driver starts yawning and makes a movement, such as a change of the posture on the seat and movement of a hand onto the face. When the level of drowsiness D is 3, it indicates that the driver is quite drowsy. In this case, the driver intentionally blinks, the blinking motion and the eye motion are both slow, the driver frequently yawns, and takes a deep breath, and the driver unnecessarily makes a movement of the body, such as shaking the head and moving the shoulders up and down. When the level of drowsiness D is 4, it indicates that the driver is very drowsy. In this case, the driver's eyelids are closed, and the head is inclined forward or backward. When the level of drowsiness D is 5, it indicates that the driver entirely falls asleep.

The state estimation portion 32 determines whether it is immediately after the start of vehicle operation, and when it is determined that it is immediately after the start of vehicle operation, the state estimation portion 32 generates the drowsiness level estimation function using the coefficients set to the default values at the time of initial process after the start of vehicle operation.

After the drowsiness level estimation function with the default coefficients is generated, the state estimation portion 32 determines whether the vehicle runs in the awakening area. In the awakening area, it is possible to consider that the driver is fully awake because of various types of external stimuli that the driver receives from the outside. The awakening area includes an awakening road section, a tension road section, and an awakening actuator operation section. When it is determined that the vehicle runs in the awakening area, such determination means that it is detected that the vehicle runs in the section where the driver is externally stimulated to increase the driver's level of wakefulness.

In the awakening road section, a facility is provided on the road to awaken the driver, and the driver is externally stimulated by a stimulus produced due to the facility provided on the road. Examples of such awakening road section include a road on which grooves are provided for the purpose of awakening the driver, and a tunnel with bright lighting provided for the same purpose. It is determined whether the vehicle runs in the awakening road section, by comparing the present position of the vehicle detected by the vehicle position detection portion 12 with the positional information of the awakening road section stored in map database. Further, the awakening road section may be detected using an external camera and a vibration sensor mounted on the vehicle.

In the tension road section, the driver sees the road circumstances and surrounding circumstances of the vehicle that make the driver tense and mentally burden the driver, and the driver is stimulated by a stimulus caused by such tension state under the road circumstances and surrounding circumstances of the vehicle as described above. Examples of the road circumstances and surrounding circumstances of the vehicle that make the driver tense include an ETC gate, traffic control, a speed monitoring device, an electronic traffic signboard, a nearby vehicle, and an emergency vehicle. If the position of the tension road section is previously determined (for example, in the cases of the ETC gate, the speed monitor device, and the electric traffic signboard), it is determined whether the vehicle runs in the tension road section, by comparing the present position of the vehicle detected by the vehicle position detection portion 12 with the positional information stored in the map database. On the other hand, if the position of the tension road section is not previously determined (for example, in the case of traffic control), it is determined whether the vehicle runs in the tension road section, by comparing the present position of the vehicle detected by the vehicle position detection portion 12 with the positional information of traffic control obtained through the vehicle information and communication system (VICS), etc. Further, if a moving body (for example, the nearby vehicle and the emergency vehicle) is the object in the tension road section, it is determined whether the vehicle runs in the tension road section using information obtained by a vehicle detection portion, a warning sound detection portion, and a radio wave receiving portion that receives radio waves generated by the emergency vehicle.

In the awakening actuator operation section, a vehicle-induced awakening actuation is performed to awaken the driver, and the stimulus produced by such vehicle-induced awakening actuation is applied to the driver. Examples of the awakening actuation include an activation of a lane keeping assist system (LKA; for example, steering assist performed by issuing a warning to the driver for avoiding departure from a lane, etc.), an activation of a lane departure warning (LDW; for example, an output of warning), an activation of a pre-crash safety system (PCS; for example, braking assist and seatbelt assist), and an activation of the awakening actuation portion 20. In the cases of LKA, LDW, and PCS, whether the vehicle runs in the awakening actuator operation section is determined based on the operational information of such systems. Further, in the case of the awakening actuation portion 20, whether the vehicle runs in the awakening actuator operation section is determined based on the operational information of the awakening actuation portion 20.

When it is determined that the vehicle runs in the awakening area, the state estimation portion 32 compares the level of drowsiness D estimated based on the plurality of blinking characteristic amounts obtained from the time-series eye-opening degree data, which are taken during the time when the vehicle runs in the awakening area (hereinafter referred to as "awakening area running time") plus a predetermined time, with the level of drowsiness D estimated based on the plurality of blinking characteristic amounts obtained from the time-series eye-opening degree data, which are taken immediately before the awakening area, in order to determine whether the awakening effect is produced. More specifically, the state estimation portion 32 determines whether the value obtained by the expression (the level of drowsiness D immediately before the awakening road section)−(the level of drowsiness D during the awakening area running time plus the predetermined time) is equal to or smaller than 0.5 in order to determine whether the awakening effect is produced. Further, the state estimation portion 32 also determines whether the level of drowsiness D estimated based on the plurality of blinking characteristic amounts obtained from the time-series eye-opening degree data during the awakening area running time plus the predetermined time is equal to 1 or smaller. Specifically, it is possible to consider that, if the vehicle runs in the awakening area, the driver is awakened by the stimulus that the driver receives in the awakening area, and therefore, the estimated level of drowsiness D is decreased from the level of drowsiness D before the awakening area, and becomes equal to or smaller than 1. If the level of drowsiness D estimated after the awakening area does not show that the awakening effect is produced, it is determined that the drowsiness level estimation function that has been used for estimating the level of drowsiness D is not adequate. Therefore, when the difference obtained by the expression (the level of drowsiness D immediately before the awakening area)−(the level of drowsiness D during the awakening area running time plus the predetermined time) is equal to or smaller than 0.5, and further, (the level of drowsiness D during the awakening area running time plus the predetermined time) is larger than 1, the state estimation portion 32 determines that the drowsiness level estimation function is not adequate, and corrects the drowsiness level estimation function.

When the vehicle runs in the awakening road section, the awakening effect is produced at different timings depending on the conditions of the awakening road section, and therefore, the determination as to whether the awakening effect is produced is made at timings as described below in accordance with the conditions of the awakening road section. If the grooves are provided on the road surface in the awakening road section, the level of drowsiness D is estimated based on the time-series eye-opening degree data taken for 20 to 30 seconds after several seconds from the time the vehicle runs over the first groove. Then, this estimated level of drowsiness D is compared with the level of drowsiness D estimated based on the time-series eye-opening degree data taken immediately before the vehicle runs over the first groove to determine whether the awakening effect is produced. In the case of the tunnel with bright lighting, if the vehicle enters the tunnel at night under the dark condition, it is relatively fast to produce the awakening effect. However, if the tunnel is long, the driver gets used to such bright circumstances and the awakening effect is gradually weakened. Therefore, the level of drowsiness D is estimated based on the time-series eye-opening degree data taken for 20 to 30 seconds after several seconds from the time when the vehicle enters the tunnel. Then, this estimated level of drowsiness D is compared with the level of drowsiness D estimated based on the time-series eye-opening degree data taken immediately before the vehicle enters the tunnel to determine whether the awakening effect is produced. If the vehicle enters the tunnel during the daytime under the bright condition, the awakening effect is less effective compared to the case where the vehicle enters the tunnel under the dark condition. However, the awakening effect still works until the driver gets used to circumstances in the tunnel, and therefore, the determination in this case is also made in a manner similar to or identical with that as described above.

When the vehicle runs in the tension road section, it is assumed that a temporary awakening effect is produced because the driver is placed under the tension state, starting at a point where an object that makes the driver tense (hereinafter referred to as "tension object") certainly comes into the sight of the driver (for example, approximately 100 m before the tension object). Based on this assumption, the level of drowsiness D is estimated based on the time-series eye-opening degree data taken from the point where the tension object comes into the sight of the driver to the point after the vehicle passes by the tension object, and this estimated level of drowsiness is compared with the level of drowsiness D estimated based on the time-series eye-opening degree data taken immediately before the vehicle enters the tension road section to determine whether the awakening effect is produced.

When the vehicle runs in the awakening actuator operation section, it is assumed that the facial expression and movement of the body of the driver instantly change immediately after the awakening actuation is performed. Based on this assumption, the level of drowsiness D is estimated based on the time-series eye-opening degree data taken for 20 to 30 seconds immediately after the awakening actuation is performed, and this estimated level of drowsiness is compared with the level of drowsiness D estimated based on time-series eye-opening degree data taken immediately before the awakening actuation is performed to determine whether the awakening effect is produced.

When it is determined that the drowsiness level estimation function needs be corrected, the state estimation portion 32 subtracts 0.5 from the level of drowsiness D estimated based on the plurality of blinking characteristic amounts obtained from the time-series eye-opening degree data taken for the awakening area running time plus the predetermined time. Then, the state estimation portion 32 recalculates the coefficient for each term of the drowsiness level estimation function so that the level of drowsiness D is equal to the result of the subtraction, and generates renewed drowsiness level estimation function using the recalculated coefficients. Alternatively, the coefficient for each term of the drowsiness level estimation function may be recalculated so that the level of drowsiness D becomes 1. However, there is a possibility that the precondition that the driver is awake after the vehicle runs through the awakening area is wrong, and therefore, the correction in the embodiment is made to this extent, that is, by subtracting 0.5 from the level of drowsiness D.

Basically, the coefficients for all the terms of the drowsiness level estimation function are subject to recalculation. However, some of the blinking characteristic amounts may change differently in the case of some types of stimuli applied to the driver, compared to the other types of stimuli. Therefore, in the case of such types of stimuli, recalculation of the coefficient for the term that represents the blinking characteristic amount that differently changes may be omitted. For example, when the driver is stimulated during the tension road section, the eye motion of the driver stays at a certain point, and the driver hardly blinks or the number of blinks is significantly reduced from the number of blinks in a normal state (this indicates that the number of blinks is obviously different in this case from that in the case of other stimuli applied). Therefore, in this case, when the coefficients are recalculated, the coefficient for the term that represents the number of blinks is kept unchanged.

For example, it is assumed that the drowsiness level estimation function has five blinking characteristic amounts (the eye-opening degree when the driver's eyes are open, an average eye-closing time per blink, the eye-closing time deviation, the total eye-closing time during unit time, and the number of blinks) as variables, and the default coefficients are set for the terms representing the blinking characteristic amounts as follows: $f_1$ (eye-opening degree when the driver's eyes are open) is 0.4; $f_2$ (average eye-closing time per blink) is 0.2; $f_3$ (eye-closing time deviation) is 0.3; $f_4$ (total eye-closing time during unit time) is 0.1; and $f_5$ (number of blinks) is 0.5. Further, it is assumed that when the level of drowsiness D is calculated from the drowsiness level estimation function with default coefficients using the blinking characteristic amounts during the awakening area running time plus the predetermined time, the level of drowsiness D is 1.5. In this case, the state estimation portion 32 subtracts 0.5 from the estimated level of drowsiness D that is 1.5, and the coefficients for the terms of the drowsiness level estimation function are recalculated so that the level of drowsiness D becomes equal to 1.0. Here, the sum of the default coefficients is equal to 1.5. Therefore, in order to reduce the level of drowsiness D from 1.5 to 1.0, the coefficients are reduced to two-thirds of the default coefficients if the coefficients are recalculated without changing the relative ratio among the terms. The coefficients are recalculated as follows: $f_1$ (eye-opening degree when the driver's eyes are open) is 0.27; $f_2$ (average eye-closing time per blink) is 0.13; $f_3$ (eye-closing time deviation) is 0.2; $f_4$ (total eye-closing time during unit time) is 0.07; and $f_5$ (number of blinks) is 0.33. In particular, in the case of the tension road section, the coefficient that represents the number of blinks is not changed. The default coefficient for the term that represents the number of blinks is 0.5, and the sum of the other default coefficients than the coefficient for the number of blinks is 1.0. Thus, in order to reduce the sum of the other coefficients from 1.0 to 0.5, if the other coefficients are recalculated without changing the relative ratio among the terms, the other coefficients need be reduced to one-half of the default values. As a result, the other coefficients are recalculated as follows: $f_1$ (eye-opening degree when the driver's eyes are open) is 0.2; $f_2$ (average eye-closing time per blink) is 0.1; $f_3$ (eye-closing time deviation) is 0.15; and $f_4$ (total eye-closing time during unit time) is 0.05. The coefficient $f_5$ (number of blinks) remains 0.5.

Every time the level of drowsiness D is estimated, the state estimation portion 32 determines whether the estimated level of drowsiness D reaches or exceeds the level of drowsiness D at which the driver needs an awakening stimulus (this level will be hereinafter referred to as "awakening stimulation level"). The awakening stimulation level functions as a threshold for determining whether the driver's wakefulness level is decreased to a low level (the driver feels strong drowsiness) such that there is a possibility, even if very low, of impairing the driver's driving operations. For example, the level of drowsiness D of "2" is set as the awakening stimulation level. When the state estimation portion 32 determines that the level of drowsiness D estimated in the present process reaches or exceeds the awakening stimulation level, the state estimation portion 32 generates an awakening actuation control signal for applying the awakening stimulus to the driver or informing the driver of the driver's current status of drowsiness, and transmits the awakening actuation control signal to the awakening actuation portion 20. The degree of the awakening stimulus applied to the driver by performing the awakening actuation may be constant, or may be increased as the level of drowsiness D becomes larger. Further, the awakening actuation portion 20 may function in a manner such that, when the level of drowsiness D is small, the awakening actuation portion 20 informs the driver of the driver's current status of drowsiness by voice, and as the level of drowsiness D is increased, the awakening actuation portion 20 applies vibration or the like to the driver.

FIG. 4 shows time-series data E1 and time-series data E2 on the results of estimation of the level of drowsiness when the vehicle runs in the awakening road section in which grooves are provided on the road surface so that vibrations are generated in a certain rhythm. The time-series data E1 indicate the results of estimation of the level of drowsiness D obtained by the corrected drowsiness level estimation function, and the time-series data E2 indicate the results of estimation the level of drowsiness D obtained by the drowsiness level estimation function without correction. When the tires go over the grooves provided on the road surface, the noise and vibration are caused and transmitted to the driver so that the driver is awakened by such noise and vibration. In particular, in Japan, it is believed that a rhythm of three-three-seven is effective for awakening the driver. The driver's wakefulness level is increased when the vehicle is running in the awakening road section and for a certain period after the vehicle passes through the awakening road section, and therefore, if the drowsiness level estimation function is corrected during such period, the drowsiness level estimation function reflects the current state of the individual driver. Therefore, after the drowsiness level estimation function is corrected, the time-series data E1 obtained by the corrected drowsiness level estimation function shows more accurate level of drowsiness (level of wakefulness) of the driver, compared to the time-series data E2 obtained by the drowsiness level estimation function without correction.

Figure 6:
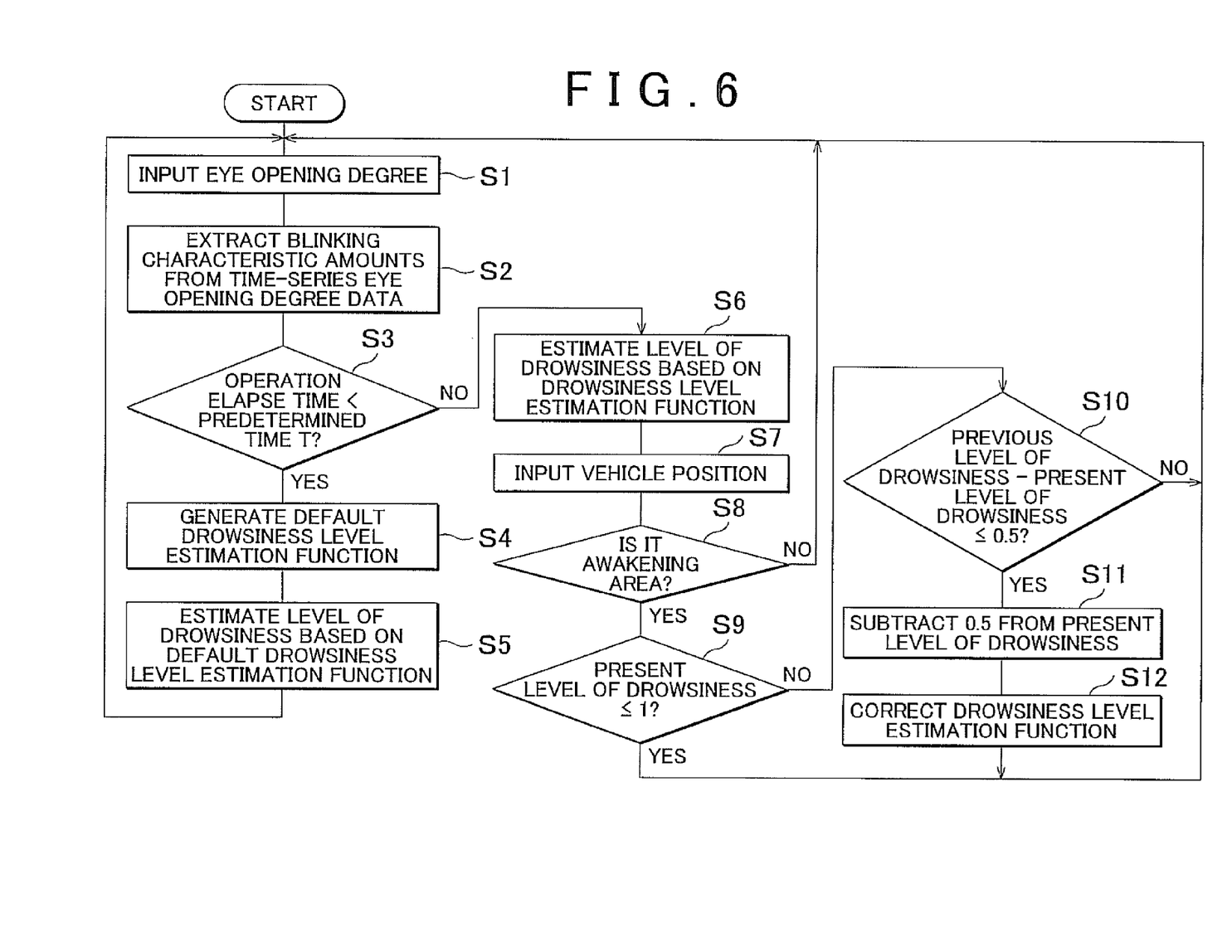
FIG. 6 is a flowchart showing a procedure performed by a state estimation portion of an ECU shown in FIG. 1.

Referring to FIG. 1, operations of the drowsiness level estimation apparatus 1 will be described. In particular, the processes performed by the state estimation portion 32 of the ECU 30 will be described referring to a flowchart shown in FIG. 6. FIG. 6 is the flowchart showing the procedure performed in the state estimation portion 32 of the ECU 30 shown in FIG. 1. The ECU 30 repeatedly performs the processes as described below at predetermined time intervals.

When the drowsiness level estimation apparatus 1 is activated, the camera 10 and the near infrared ray projector 11 are also activated. The near infrared ray projector 11 projects the near infrared rays toward the region around the driver's face. The camera 10 captures an image of the region including the driver's face at predetermined time intervals, and outputs the captured image to the ECU 30. Further, the vehicle position detection portion 12 detects the present position of the vehicle at predetermined time intervals and outputs information on the detected position of the vehicle to the ECU 30.

The ECU 30 receives the images from the camera 10. The image processing portion 31 of the ECU 30 detects the position of the driver's face in the image, and extracts the eye, the nose, and the mouth of the driver, which are components of the face, from the portion of the image including the driver's face. Further, the region including the driver's eye is further searched to detect the shape of the eyelid, and the eye-opening degree is obtained based on the detection result of the eyelid shape. The state estimation portion 32 of the ECU 30 receives the eye-opening degree obtained by the image processing portion 31 and buffers the time-series eye-opening degree data taken for a predetermined period of time (S1).

Then, the state estimation portion 32 analyzes the time-series eye-opening degree data and extracts the plurality of blinking characteristic amounts (S2).

The time counting portion 33 counts an operation elapse time, which is the time elapsed after the start of vehicle operation, and the state estimation portion 32 determines whether the operation elapse time is smaller than a predetermined time T (S3). When it is determined in S3 that the operation elapse time is smaller than the predetermined time T, the state estimation portion 32 generates the drowsiness level estimation function that has a default value, which is set by statistically determining the coefficients for the terms of the drowsiness level estimation function that represent the respective blinking characteristic amounts (S4). Then, the state estimation portion 32 estimates the level of drowsiness D using the extracted blinking characteristic amounts based on the drowsiness level estimation function having the default value (S5).

When it is determined in S3 that the operation elapse time is equal to or larger than the predetermined time T, the state estimation portion 32 estimates the level of drowsiness D in the present process using the extracted blinking characteristic amounts based on the drowsiness level estimation function (default or corrected) set in the previous calculation (S6). Further, the ECU 30 receives the detected present position of the vehicle, and the present position of the vehicle is input to the state estimation portion 32 (S7).

The state estimation portion 32 determines whether the vehicle runs in the awakening area based on the vehicle position, etc (S8). When it is determined in S8 that the vehicle does not run in the awakening area, the drowsiness level estimation function is not corrected.

When it is determined in S8 that the vehicle runs in the awakening area, the state estimation portion 32 determines whether the level of drowsiness D estimated in the present process is equal to or smaller than 1 (S9). When it is determined in S9 that the level of drowsiness D estimated in the present process is equal to or smaller than 1, this indicates that the level of drowsiness D is properly determined in the present process using the drowsiness level estimation function that is currently set, and therefore, the drowsiness level estimation function is not corrected. It should be noted that the value "1" used herein is just an example, and the value is not limited to this example value.

When it is determined in S9 that the level of drowsiness D is larger than 1, the state estimation portion 32 determines whether the value obtained by the expression (the level of drowsiness D estimated in the previous process–the level of drowsiness D estimated in the present process) is equal to or smaller than 0.5 (S10). When it is determined in S10 that the value obtained by the expression (the level of drowsiness D estimated in the previous process–the level of drowsiness D estimated in the present process) is larger than 0.5, it is determined that the driver's level of wakefulness is properly estimated with good follow-up characteristics with the use the drowsiness level estimation function that is currently set. Therefore, the drowsiness level estimation function is not corrected.

When it is determined in S10 that the value obtained by the expression (the level of drowsiness D estimated in the previous process–the level of drowsiness D estimated in the present process) is equal to or smaller than 0.5, it is determined that the level of drowsiness D is not properly estimated using the drowsiness level estimation function that is currently set. Therefore, the state estimation portion 32 subtracts 0.5 from the level of drowsiness D estimated in the present process, and re-set the result of the subtraction as the level of the drowsiness D estimated in the present process (S11). Then, the state estimation process 32 recalculates the coefficients for the terms of the drowsiness level estimation function so that the level of drowsiness D becomes equal to the re-set value, and the drowsiness level estimation function is corrected using the recalculated coefficients (S12). It should be noted that the value "0.5" used in the determination and subtraction herein is just an example, and such values are not limited to the value "0.5". Further, the value subtracted may be set to a value that varies depending on the levels of the drowsiness D, instead of a constant value such as 0.5. This is because there are some cases where, even in the same awakening road section or the tension road section, the sensitivity of the driver may vary depending on the level of drowsiness D, and therefore the awakening effect is not produced in some cases. In an extreme case, when a weak warning is issued to the driver who is asleep, it is possible that the driver does not notice such weak warning at all. In this case, it is not appropriate to forcibly correct the level of drowsiness D by subtraction. Setting different values to be subtracted in accordance with the level of drowsiness D may be performed in a stepwise manner, may be performed by providing a certain threshold, or may be performed using these methods, depending on the type of awakening stimulus as well.

The state estimation portion 32 determines whether the level of drowsiness D estimated in the present process is equal to or larger than the awakening stimulation level. Then, when it is determined that the level of drowsiness D estimated in the present process is equal to or higher than the awakening stimulation level (that is, the level of wakefulness of the driver is decreased to a low level such that there is a possibility, even if very low, of impairing the driving operations), the state estimation portion 32 sets the awakening actuation control signal and outputs the awakening actuation control signal to the awakening actuation portion 20 so as to awaken the driver.

When the awakening actuation portion 20 receives the awakening actuation control signal, the awakening actuation portion 20 is operated in accordance with the awakening actuation control signal. In this way, the awakening stimulus produced by operating the awakening actuation portion 20 is applied to the driver, and the driver's level of wakefulness is increased. As a result, the driver pays more attention to driving.

According to the drowsiness level estimation apparatus 1, the awakening area in which the driver is externally stimulated is detected, and the drowsiness level estimation function is corrected when the driver is awakened by the stimulus produced in the awakening area. This makes it possible to generate the drowsiness level estimation function that matches the current state of the driver, and estimate the driver's level of drowsiness with high accuracy based on the drowsiness level estimation function thus generated. Such highly accurate estimation of the driver's level of drowsiness makes it possible to determine whether the driver's level of wakefulness is decreased with high accuracy, and further, it is possible to perform the actuation to awaken the driver at appropriate timings. Further, it is also possible to reduce the actuation performed at inappropriate timings, and therefore, it is possible to reduce the chances that the driver feels discomfort with and distrust toward the actuation performed.

Further, in the drowsiness level estimation apparatus 1, even in the case of the awakening area, it is possible to more appropriately correct the drowsiness level estimation function by determining whether the awakening effect is produced, based on the level of drowsiness estimated using the drowsiness level estimation function, and correcting the drowsiness level estimation function only when it is determined that the estimated level of wakefulness does not reflect the awakening effect.

In particular, in the drowsiness level estimation apparatus 1, when the vehicle runs in the tension road section, because the number of blinks is significantly decreased compared to the number of blinks when the vehicle runs in other road sections in the awakening area, the coefficient for the term that represents the number of blinks is not changed. Accordingly, it is possible to more appropriately correct the drowsiness level estimation function.

An embodiment of the invention has been described as above. However, the invention is not limited to the embodiment as described above, and may be embodied in various modifications and variations.

For example, in the embodiment, the wakefulness level estimation apparatus is employed as the apparatus that is installed in a vehicle and estimates the level of drowsiness (level of wakefulness) of the driver of the vehicle. However, the wakefulness level estimation apparatus may be used for estimating the level of wakefulness of various types of people, such as drivers of other types of vehicles, monitoring staffs of plants, and night-shift workers.

Further, in the embodiment, the blinking characteristic amounts, such as the eye-opening degree and the number of blinks, are used as the wakefulness level correlation values. However, the wakefulness level correlation value may be other physiological information, such as the eye direction, the heart-rate condition, the breathing condition, the brain wave condition, or the electro-dermal activity, and may be a combination of a plurality of types of physiological information.

Further, in the embodiment, the external stimulus applied to the driver is the stimulus applied to the driver when the vehicle runs in the awakening road section, the tension road section, or the awakening actuator operation section. However, the external stimulus may be other stimulus that is externally applied to the driver. If the subject person of the wakefulness level estimation is any other occupant than the driver, the external stimulus may be the stimulus that is externally applied to the subject person.

Further, in the embodiment described above, it is determined whether the vehicle runs in the awakening road section or in the tension road section based on the present position of the vehicle and the map data. However, the determination as to whether the vehicle runs in the awakening road section or in the tension road section may be made by using other means. For example, in the case of the tunnel that is provided with bright lighting for the purpose of awakening the driver, the determination may be made by detecting the external light of the vehicle. Further, in the case of the grooves provided on the road surface for the purpose of awakening the driver, the determination may be made by detecting the vibration of the vehicle.

Further, in the embodiment as described above, the level of drowsiness is estimated based on the drowsiness level estimation function using the blinking characteristic amounts (wakefulness level correlation value), such as the eye-opening degree, as variables, and the coefficients used for the drowsiness level estimation function are corrected in the case of the awakening area. However, the level of wakefulness may be estimated based on a difference between the wakefulness level correlation value and a reference value of the wakefulness level correlation value, and the reference value of the wakefulness level correlation value may be corrected in the case of the awakening area.

Further, in the embodiment as described above, the drowsiness level estimation function is corrected based on the data taken when the driver's level of wakefulness is increased during the awakening area or after the awakening area. However, when it is determined that the driver's level of wakefulness is certainly decreased when the vehicle runs in the awakening actuator operation section, the drowsiness level estimation function may be corrected based on the data taken when the level of wakefulness is certainly decreased. For example, when the driver is astonished and recovers senses due to the actuation performed, such as LKA and LDW, or beeping of a cellular phone or a wireless phone, it is determined that the driver's level of wakefulness has been significantly low until such system or instrument is operated. If the level of drowsiness estimated immediately before the operation of such system or instrument is smaller than 3 (in other words, if it can be determined that the estimated level of drowsiness is not correct), the drowsiness level estimation function may be retroactively corrected so that the level of drowsiness estimated immediately before the operation of the system or the instrument is corrected to be 3 or larger.

Further, in the embodiment, at the start of the vehicle operation, the default drowsiness level estimation function statistically determined is generated. However, the invention may be configured as follows: at the time of the start of operation, the driver is authorized using, for example, the image of the driver captured by the camera, or the driver is identified by an input made by the driver, and, if the drowsiness level estimation function learned (corrected) in the past with respect to the driver is available, the past drowsiness level estimation function is read out, and the drowsiness level estimation function is individually set for the driver based on the past drowsiness level estimation function.

While the invention has been described with reference to example embodiments thereof, it should be understood that the invention is not limited to the example embodiments or constructions. To the contrary, the invention is intended to cover various modifications and equivalent arrangements. In addition, while the various elements of the example embodiments are shown in various combinations and configurations, which are exemplary, other combinations and configurations, including more, less or only a single element, are also within the spirit and scope of the invention.

What is claimed is:

1. A wakefulness level estimation apparatus, comprising: an ECU having:
   an estimation portion operable to estimate a level of wakefulness of a subject person based on one of a wakefulness level estimation function, of which a variable is a wakefulness level correlation value of the subject person, and a difference between the wakefulness level correlation value of the subject person and a reference value of the wakefulness level correlation value;
   a stimulation detection portion operable to detect whether an awakening stimulation is externally applied to the subject person and operable to detect that the stimulation is externally applied to the subject person when a vehicle runs in an area in which an awakening effect is produced by the stimulation being externally applied to the subject person, the area being one of (i) an area in which a facility is provided on a road to produce the awakening effect on the subject person, (ii) an area in which a tension stimulus is applied to the subject person due to a change of road circumstances and surrounding circumstances of the vehicle, and (iii) an area in which a physical stimulus that produces the awakening effect is applied to the subject person; and
   a correction portion that, when the stimulation detection portion detects that the awakening stimulation is applied to the subject person, is operable to compare a level of wakefulness of the subject person estimated by the estimation portion after the simulation detection portion detects that the awakening stimulation is externally applied to the subject person with a level of wakefulness of the subject person estimated by the estimation portion before the stimulation detection portion detects that the awakening stimulation is externally applied to the subject person, and is operable to repeatedly perform a correction of one of the reference value of the wakefulness level correlation value and the wakefulness level estimation function, which is used for estimating the level of wakefulness of the subject person based on result of comparison of the level of wakefulness after the stimulation and the level of wakefulness before the stimulation, so as to make the level of wakefulness after the stimulation higher than the level of wakefulness before the stimulation.

2. The wakefulness level estimation apparatus according to claim 1, further comprising:
   an awakening actuation portion operable to apply the stimulation externally applied to the subject person;
   wherein the stimulation externally applied to the subject person is provided by a plurality of stimuli including the tension stimulus;
   the wakefulness level correlation value includes a plurality of blinking characteristic amounts including a number of blinks; and
   when the stimulation detection portion detects that the subject person is externally stimulated by the tension stimulus, the correction portion performs the correction in a manner different from a manner when the subject person is stimulated by another stimulus than the tension stimulus.

3. The wakefulness level estimation apparatus according to claim 2, wherein when the stimulation detection portion detects that the subject person is stimulated by the tension stimulus, the correction portion performs the correction without changing a value pertaining to the number of blinks, which is one of the blinking characteristic amounts.

4. The wakefulness level estimation apparatus according to claim 1, wherein the level of wakefulness of the subject person is determined based on an eye-opening degree of the subject person.

5. The wakefulness level estimation apparatus according to claim 1, wherein when the stimulation detection portion detects that the stimulation is externally applied to the subject person, the correction portion corrects the wakefulness level estimation function when the level of wakefulness of the subject person estimated based on the wakefulness level estimation function does not reach a level of wakefulness at which it is determined that the subject person has been waken by the awakening stimulation.

6. The wakefulness level estimation apparatus according to claim 1, wherein the wakefulness level estimation apparatus is mounted on the vehicle, and the stimulation detection portion detects that the stimulation is externally applied to the subject person when the vehicle runs in an area that the awakening effect is produced by the stimulation externally applied to the subject person.

7. The awakening level estimation apparatus according to claim 6, wherein the area that the awakening effect is produced by the stimulation externally applied to the subject person is an area in which a facility is provided on a road to produce the awakening effect on the subject person.

8. The awakening level estimation apparatus according to claim 6, wherein the area that the awakening effect is produced by the stimulation externally applied to the subject person is an area in which the tension stimulus is applied to the subject person due to a change of road circumstances and surrounding circumstances of the vehicle.

9. The wakefulness level estimation apparatus according to claim 8, wherein:
   the wakefulness level correlation value includes a plurality of blinking characteristic amounts including a number of blinks; and
   when the stimulation detection portion detects that the subject person is stimulated by the tension stimulus, the correction portion performs the correction without changing a value pertaining to the number of blinks, which is one of the blinking characteristic amounts.

10. The wakefulness level estimation apparatus according to claim 6, wherein the area that the awakening effect is produced by the stimulation externally applied to the subject person is an area in which a physical stimulus that produces the awakening effect is applied to the subject person.

11. The wakefulness level estimation apparatus according to claim 1, wherein the stimulation is a tension stimulus.

12. The wakefulness level estimation apparatus according to claim 11, wherein the tension stimulus increases the level of wakefulness of the subject person.

13. The wakefulness level estimation apparatus according to claim 12, wherein the tension stimulus is applied to a driver by at least one of a change of road circumstances, surrounding circumstances of the vehicle and a vehicle induced awakening actuation.

14. The wakefulness level estimation apparatus according to claim 1, wherein the correction portion performs the correction of one of the reference value of wakefulness level correlation value and the wakefulness level estimation function when a difference between:
  (a) the level of wakefulness estimated when the simulation detection portion detects that the awakening stimulation is externally applied to the subject person, and
  (b) the level of wakefulness estimated before the simulation detection portion detects that the awakening stimulation, is externally applied to the subject person and is equal to or smaller than a first predetermined value.

15. The wakefulness level estimation apparatus according to claim 1, wherein the correction portion performs the correction of one of the reference value of wakefulness level correlation value and the wakefulness level estimation function when:
  (i) a difference between:
    (a) the level of wakefulness estimated when the simulation detection portion detects that the awakening stimulation is externally applied to the subject person, and
    (b) the level of wakefulness estimated before the simulation detection portion detects that the awakening stimulation, is externally applied to the subject person and is equal to or smaller than a first predetermined value, and
    (ii) the level of wakefulness estimated when the simulation detection portion detects that the awakening stimulation is externally applied to the subject person is larger than a second predetermined value which is larger than the first predetermined value.

16. The wakefulness level estimation apparatus according to claim 1, wherein the correction portion resets the level of wakefulness estimated when the simulation detection portion detects that the awakening stimulation is externally applied to the subject person by subtracting a certain value from the level of wakefulness, and repeatedly performs the correction of one of the reference value of wakefulness level correlation value and the wakefulness level estimation function so that the level of wakefulness becomes equal to the reset level of wakefulness.

* * * * *